US00PP09749P

United States Patent [19]

Pouw

[11] Patent Number: Plant 9,749

[45] Date of Patent: Dec. 17, 1996

[54] MINIATURE ROSE PLANT NAMED 'RUIFIRE'

[75] Inventor: Antonius A. Pouw, Hazerswoude, Netherlands

[73] Assignee: De Ruiter's Nieuwe Rozen B.V., Hazerswoude, Netherlands

[21] Appl. No.: 562,973

[22] Filed: Nov. 24, 1995

[51] Int. Cl.[6] ..... A01H 5/00

[52] U.S. Cl. ..... Plt./7.1

[58] Field of Search ..... Plt./7.1, 10.1, 8.2

[56] References Cited

U.S. PATENT DOCUMENTS

P.P. 4,659 3/1981 Christensen ..... Plt./7.1

*Primary Examiner*—Howard J. Locker

*Attorney, Agent, or Firm*—Proprietary Rights International

[57] ABSTRACT

A distinctive cultivar of miniature rose plant named Ruifire, characterized by its large yellow and organe bi-color flowers; numerous flowers per plant; long shelf-life; and strong rooting habit.

2 Drawing Sheets

The present invention relates to a new and distinct cultivar of the miniature rose class, botanically known as *Rosa hybrida,* and hereinafter referred to by the cultivar name Ruifire.

The new cultivar is a product of a planned breeding program conducted by the inventor in Hazerswoude, The Netherlands. The objective of the breeding program was to develop compact pot rose varieties with garden performance that can be asexually reproduced by cuttings. The new cultivar originated from a cross made by the inventor in 1990 of two unnamed proprietary seedlings. The cultivar Ruifire was discovered and selected by the inventor as a flowering plant within the progeny of the stated cross in a controlled environment in Hazeswoude, The Netherlands.

Asexaul reproduction of the new cultivar by cuttings taken at Hazerswoude, The Netherlands, has shown that the unique features of this new miniature rose plant are stable and reproduced true to type in successive generations of asexual reproduction.

The following traits have been repeatedly observed and are determined to be the unique characteristics of Ruifire. These characteristics in combination distinguish the new miniature rose plant as a new and distinct cultivar:

1. Large yellow and orange bi-color flowers.
2. Numerous flowers per plant.
3. Long shelf-life.
4. Strong rooting habit.

The new miniature rose plant has not been observed under all possible environmental conditions. The phenotype may vary significantly with variations in environment such as temperature and light level, without, however, any variance in genotype.

The accompanying colored photographs illustrate typical specimens of the vegetative growth and flowers of the new miniature rose plant, showing the colors as true as it is reasonably possible to obtain in colored reproductions of this type.

The first photograph comprises a side perspective view of a typical plant of the new miniature rose plant grown in Hazerswoude, The Netherlands. In this photograph, the flower color appears lighter than the actual due to light reflectance.

The second photograph comprises details of the new miniature rose plant. In this photograph the top of a young shoot (1); a leaf with three leaflets (2); a leaf with five leaflets (3); a leaf with seven leaflets (4); a stem with prickles (5); a flower bud after sepals open (6); a flowr bud after petals begin to unfurl (7); a flower one-third to one-half open (8); a flower fully open (9); a flower stem with sepals, stamens and pistils (10); a flower stem with sepals and pistils (11); and a flower stem with pistils only (12) are shown.

The following observations, measurements, values, and comparisons describe plants grown in Hazerswoude, The Netherlands, under glass covering with average day temperatures of 20° C., average night temperatures of 16° to 18° C., and an average light level of 2,000 J/cm$^2$.

In the following description, color references are made to The Royal Horticultural Society Colour Chart except where general terms of ordinary dictionary significance are used.

Classification:

*Botanical.*—*Rosa hybrida* cultivar Ruifire.

*Commercial.*—Miniature pot rose.

Parentage:

*Male or pollen parent.*—Unnamed proprietary seedling.

*Female or seed parent.*—Unnamed proprietary seedling.

Plant Description

Form: Rounded form, uniform, and spreading.

Growth habit: Moderately vigorous yet compact. Freely branching, dense growth. Suitable for 10-cm containers. Time to produce a finished plant in a 10-cm container 20 to 30 cm in height is generally 10 to 12 weeks depending on average temperature, light level, and cultural practices.

Stem and lateral branches:

*Quantity of lateral branches from pinching.*—Generally three.

*Lenth of lateral branches.*—1 to 5 cm.

*Color.*—144A.

Foliage description: Leaves arranged alternately, compound with three to seven leaflets per leaf, generally symmetrical, abundant, and flat in aspect. Stipules at leaf base.

*Quantity.*—Five to eight per lateral branch.

*Leaflet size.*—Length: 2 to 2.5 cm. Width: 1.5 to 2 cm.

*Shape.*—Ovate with acute tip and obtuse base.

*Texture.*—Smooth and glossy.

*Margin.*—Serrate.

*Petiole length.*—2 cm.

*Color.*—Young foliage, upper side: 137C. Young foliage, under side: 137D. Mature foliage, upper side: 137A. Mature foliage, under side: 138B. Petiole: 144A. Stipule: 144A. Venation, upper side: 144B. Venation, under side: 144A.

Prickles: Located on petioles and stems.
*Length.*—Immature: 0.1 cm. Mature: 0.6 cm.
*Color.*—Immature: 150C. Mature: 172B.

Flower Description

Flower type and habit: Large yellow and orange bi-color flowers. Consistently symmetrical rosette flowers that are flat in aspect. Freely and continuously flowering. The flowers are borne singly on peduncles and arranged in clusters of three to nine flowers each. There are numerous sprays per plant.
Flowering season: Year-round under greenhouse conditions, optimal flowering during summer and autumn in the Northern Hemisphere.
Flower diameter: 2 to 4 cm.
Flower depth (height): 1 to 2 cm.
Flower longevity on plant: 15 days.
Fragrance: Very slight.
Persistent: Yes.
Flower buds:
*Shape.*—Ovoid.
*Size.*—Length: 1 to 1.2 cm. Width: 0.5 to 1 cm.
*Color.*—144A.
Petals:
*Quantity.*—At least 25 per flower.
*Arrangement.*—Five rows of petals with five petals each.
*Size.*—Length: 1.5 to 2 cm. Width: 1.2 to 1.4 cm.
*Shape.*—Ovate with obtuse tip.
*Texture.*—Smooth and velvety.
*Margin.*—Entire.
*Color.*—When opening: 24C with 39B at margin. Upper side, mature: 13C with 31B at margin. Under side, mature: 13C with 31A margin. Fade: Upper and under sides fade to 36D with 38A at margin.
Petaloids:
*Quantity.*—20 to 50 per flower.
*Arrangement.*—Four to 10 rows of petals with five petaloids each.
*Size.*—Length: 0.2 to 1.5 cm. Width: 0.1 to 1 cm.
*Shape.*—Elliptical with obtuse tip.
*Textile.*—Smooth and satiny.
*Margin.*—Entire.
*Color.*—Immature: 15A with 34B at margin. Mature: 13C with 31B at margin.
Sepals:
*Quantity.*—Five per flower.
*Arrangement.*—One row with five sepals.
*Shape.*—Narrowly ovate with acute tip.
*Texture.*—Pubescent.
*Color.*—Upper side: 144A. Under side: 144A with 139D at base
Calyx:
*Size.*—0.5 cm.
*Shape.*—Funnel.
*Color.*—144A.
Peduncles: Strong and erect, pubescent.
*Length.*—3.5 to 4 cm.
*Color.*–144A.
Reproductive organs:
*Stamens.*—Quantity: 50 to 60 per flower. Anther size: 0.1 cm. Anther shape: Oblong. Anther color: 21A.
*Pistils.*—Quantity: 40 to 50 per flower. Style length: 0.3 cm. Style color: 39A. Stigma color: 161D.
Disease resistance: No resistance or susceptibility observed.
Seed production: Seed production is rarely observed.

It is claimed:

1. A new and distinct miniature rose plant named Ruifire, as illustrated and described.

* * * * *

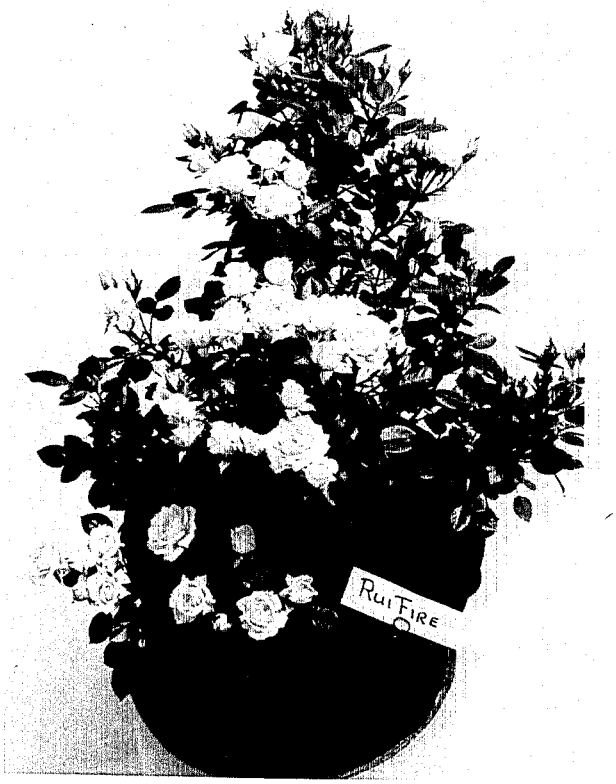
RuiFire

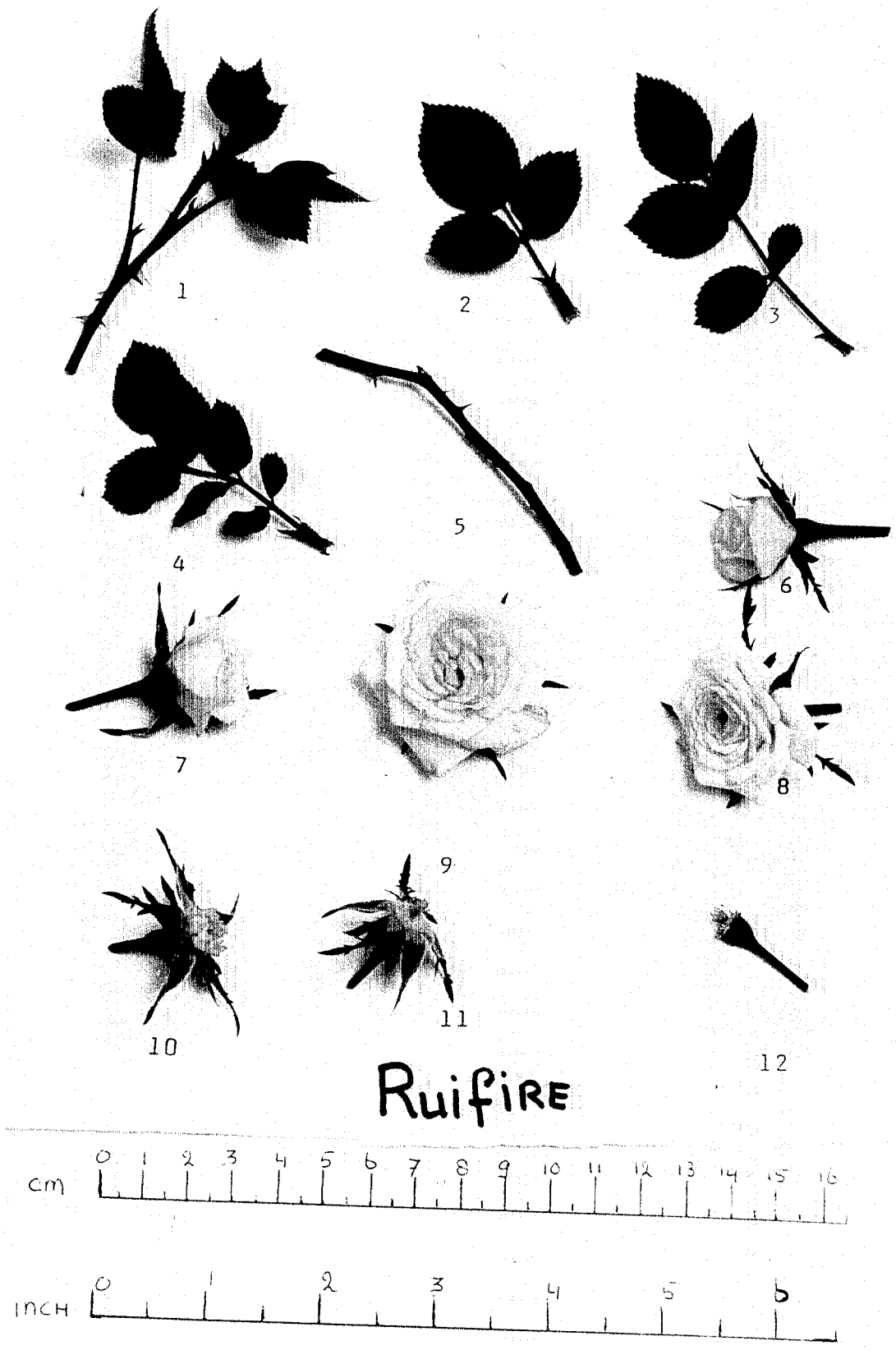
1
2
3
4
5
6
7
8
9
10
11
12
Ruifire
cm
0 1 2 3 4 5 6 7 8 9 10 11 12 13 14 15 16
INCH
0 1 2 3 4 5 6